United States Patent
Janzek-Hawlat et al.

(10) Patent No.: US 8,946,162 B2
(45) Date of Patent: Feb. 3, 2015

(54) TREATMENT OF TUMORS

(76) Inventors: Evelyne Janzek-Hawlat, Vienna (AT); Hans Loibner, Vienna (AT); Manfred Schuster, Schrick (AT); Bernhard Peball, Vienna (AT)

(*) Notice: Subject to any disclaimer, the term of this patent is extended or adjusted under 35 U.S.C. 154(b) by 536 days.

(21) Appl. No.: 12/937,029

(22) PCT Filed: Apr. 7, 2009

(86) PCT No.: PCT/AT2009/000136
§ 371 (c)(1),
(2), (4) Date: Oct. 8, 2010

(87) PCT Pub. No.: WO2009/124330
PCT Pub. Date: Oct. 15, 2009

(65) Prior Publication Data
US 2011/0033524 A1    Feb. 10, 2011

(30) Foreign Application Priority Data
Apr. 9, 2008 (AT) .................. A 566/2008

(51) Int. Cl.
*A61K 38/48* (2006.01)
*A61K 9/00* (2006.01)

(52) U.S. Cl.
CPC ..... *A61K 38/4813* (2013.01); *C12Y 304/17023* (2013.01); *A61K 9/0019* (2013.01)
USPC ........................................ 514/16.3

(58) Field of Classification Search
CPC ................................ A61K 38/4813
See application file for complete search history.

(56) References Cited

U.S. PATENT DOCUMENTS

2003/0203834 A1* 10/2003 Tallant et al. ............. 514/1
2005/0147600 A1* 7/2005 Acton et al. ............. 424/94.64
2008/0159962 A1* 7/2008 Penninger et al. ............. 424/45

FOREIGN PATENT DOCUMENTS

WO    WO 00/18899    4/2000
WO    WO 2004/000367    12/2003

OTHER PUBLICATIONS

Deshayes et al. Trends in Endocrinology and Metabolism, 2005, vol. 16, No. 7, pp. 293-299.*
Anandanadesan et al. J. Gastrointest. Surg., 2008, vol. 12, pp. 57-66 (Published Online Nov. 17, 2007).*
Suganuma et al. Clinical Cancer Research, 2005, vol. 11, pp. 2686-2694.*
Loibner, et al., Development of recombinant human soluble angiotensin converting enzyme 2 (rkACE2) for cancer therapy., Proceedings of the American association for cancer research annual meeting, bd. 49, Apr. 2008.
Deshayes, et al., Angiotensin receptors: a new role in cancer? Trends in Endocrinology & Metabolism, vol. 16, No. 7, Sep. 2005, pp. 293-299.
Tipnis, et al., A Human Homolog of Angiotensin-converting Enzyme. J. Biol. Chem., vol. 275, No. 43, Oct. 27, 2000, pp. 33238-33243.

* cited by examiner

*Primary Examiner* — James D Anderson
(74) *Attorney, Agent, or Firm* — Jason C. Fedon; William T. Han

(57) ABSTRACT

The invention provides for innovative improvements in tumor therapy, particularly therapies which are conducted using endogenous substances and which have no or only mild side-effects. Accordingly the present invention relates to methods of treating or preventing tumor diseases other than lung cancer comprising administering a polypeptide with an angiotensin-converting-enzyme-2 (ACE2) activity.

9 Claims, No Drawings

TREATMENT OF TUMORS

This application is a 371 of International Application No. PCT/AT2009/000136, filed 7 Apr. 2009, which claims priority to A566/2008, filed 9 Apr. 2008, all of which are herein incorporated by reference in their entireties.

The invention relates to the treatment of tumours.

According to information from the American Cancer Society 5.4 million people are diagnosed with cancer each year in industrialised countries and a total of 6.7 million in less developed countries, which means that the number of new cancer cases has now risen to over 12 million per annum. A total of 7.7 million people worldwide currently die each year from a tumour. The three most common cancers in industrialised countries are tumours of the prostate, lung and bowel, with women suffering most commonly from breast, bowel and lung cancer. Since infections have become controllable and people are living for longer, cancer is occupying an increasingly higher position in the mortality statistics of industrialised countries.

The picture is changing in developing countries: here lung, stomach and liver cancer are the most common cancers in men. Women suffer most often from breast, cervical and stomach cancer. Stomach and cervical cancer are generally the result of an infection.

In total, 15 percent of all cases of cancer are attributable to pathogens, with people living in developing countries being affected more frequently. For them, 26 percent of tumours are the result of infections, whereas in industrialised countries the figure is only 6 percent.

In Austria, as in other industrialised countries, cancer is the second most common cause of death, surpassed only by cardiovascular disease. In Germany around 395,000 people develop cancer each year, and of these around 195,000 are women and 200,000 men. Most cases occur over the age of 60 years. People under the age 60, at around 107,000 cases, account for about a quarter of new cancer cases.

Many tumour therapies, such as radiotherapy, chemotherapy or surgical removal of tumours, have been established for years and are constantly being refined and improved. New therapies include immunotherapies, therapies aimed at angiogenesis or at specific tumour cell markers, e.g. using monoclonal antibodies.

Despite the improved treatment opportunities for many tumours that have been developed in the last 30 years, the fight against cancer has not been won, as was expected to happen in the near future at the start of the 1970s.

Even in industrialised countries the current cure rate for cancer is around 30 to 65 percent (USA: 65 percent), grouping together all the different cancers for both sexes. In individual cases, however, the chances of cure are widely different: the chances are often good as long as the cancer remains localised; if the tumour has already spread to several organs of the body, the chances are considerably lower. In general the early detection of cancer is extremely important. Also, patients can respond differently to chemotherapy, and for some patients certain classes of active substance are completely or almost completely ineffective.

Both U.S. Pat. Nos. 6,194,556 and 7,482,171 (both incorporated herein by reference) describe ACE2 nucleic acid and amino acid sequences, functional variants and assays to determine ACE2 activity.

Zhou et al. (Tohoku J. Exp. Med. 217 (2009): 123-131; incorporated herein by reference) describe changes in Ang II concentration and ACE2 expression values in adenocarcinoma tissue of the pancreas (pancreatic ductal adenocarcinoma—PDAC). It was found that Ang II accumulates in PDAC cell lines and down-regulates the expression of ACE2 protein. Attention was drawn in that document to the fact that the ratio of ACE/ACE2 is of particular importance and an imbalance in that ratio can result in various diseases and is involved in the pathogenesis of PDAC. Therefore ACE2 was proposed as a molecular target for the treatment of PDAC.

A particular problem of many treatment methods are the severe side-effects. Often cancer patients die not because of the tumour, but because of the substances and methods used to fight the tumour.

There is therefore still a great need for innovative improvements in tumour therapy, particularly therapies which are conducted using endogenous substances and which have no or only mild side-effects. It is therefore the problem of the present invention to make available tumour therapies that are efficient and have no or at least no severe side-effects.

Accordingly the present invention relates to the use of a polypeptide with angiotensin-converting enzyme 2 (ACE2) activity for the production of a medicament for the treatment of tumours, with the exception of lung cancer.

According to the present invention tumours are treated with ACE2 activity. It was found that ACE2 activity is able to stop tumour cell growth efficiently without the fear of side-effects because of this activity.

For decades it was mainly functions of homeostasis and in particular blood pressure regulation that were ascribed to the renin angiotensin system (RAS). During the last few years, however, further properties of the RAS have been recognised and its sphere of activity has been expanded by essential functions such as that of cell proliferation, angiogenesis, inflammation and pathological changes in tissue structure. A key peptide of the "activated" RAS is angiotensin II (Ang II) which as a positive regulator of the RAS has vasoconstrictive, hypertensive, pro-inflammatory, proliferative and pro-angiogenetic properties. In addition, Ang II assists in the formation of reactive superoxides. All these properties favour cellular degeneration and contribute to the formation of malignant daughter cells. Thus, the degenerated cell uses vascularisation to grow into a primary tumour. It has been found that Ang II is present in increased quantities in various solid tumours.

The enzyme crucially responsible for the production of Ang II is the angiotensin-converting enzyme (ACE) which converts the decapeptide angiotensin I to Ang II. As part of a blood-pressure regulating cascade (again of the RAS), ACE occupies a central position particularly in the regulation of blood pressure. High ACE activity increases the tonicity of blood vessels and hence blood pressure. Inhibition of ACE is therefore a successful therapeutic approach for the treatment of high blood pressure (hypertension). ACE inhibitors, such as captopril, enalapril, lisinopril and ramipril, are some of the biggest selling drugs ever. On the basis of the above considerations ACE inhibitors have therefore also been proposed and used for a considerable time in the area of tumour therapy.

In this connection it has also been shown that besides an increased concentration of Ang II its receptors AT1 and AT2 (AT1R and AT2R) are significantly overexpressed in many solid tumours. Ang II makes a significant contribution here to tumour neovascularisation and from there to tumour invasion. It also promotes mitogen-activated protein (MAP) kinase phosphorylation and VEGF secretion. Both mechanisms have been recognised as relevant in the formation and supply of solid tumours. Clinically, increased AT1R expression correlates with increased VEGF titres and a significantly reduced prognosis of survival.

Therefore, subsequent to ACE inhibitors, the increasing number of AT1R antagonists (i.e. specific inhibitors of the angiotensin II subtype 1 receptor, the stimulation of which by Ang II results in a hypertensive effect), such as e.g. losartan, valsartan, candesartan, eprosartan, irbesartan, telmisartan or olmesartan, has also been proposed in the area of tumour therapy.

Despite their (commercial) success in the area of lowering blood pressure the use of ACE inhibitors or AT1R antagonists is also associated with disadvantages, e.g. their side-effects, which in some cases are severe.

The tumour therapy concepts proposed on the basis of ACE inhibitors or AT1R antagonists have not so far caught on, even though such proposals were made shortly after development of the first ACE inhibitors (captopril 1974; marketed since 1981) or AT1R antagonists (losartan marketed since 1996). Even though this mechanism appears at least to be scientifically interesting, successful practical use in clinical tumour therapy has not so far been achieved on a broad basis.

A further essential effector peptide of the RAS is angiotensin 1-7 (Ang 1-7). This peptide is the perfect antagonist for Ang II: whereas Ang II is a positive regulator of the RAS, Ang 1-7 can be regarded as a negative RAS modulator. Ang 1-7 attenuates the effects of Ang II and has antihypertensive, anti-inflammatory, antiproliferative, anti-angiogenetic and vasodilatory properties. It activates NO synthetase and also reduces the expression of the AT1 receptor. Ang 1-7 also inhibits MAP kinase phosphorylation induced by Ang II. In addition, Ang 1-7 prevents in vitro the growth of lung cancer cell lines and, in experimental tumour models in mice, the growth of tumours. Interestingly ACE, the enzyme crucially responsible for the production of Ang II, is inhibited by Ang 1-7. Ang 1-7 therefore prevents the synthesis of its antagonist Ang II. It has also been proposed to use Ang 1-7 for tumour therapy, however owing to the short half-life of this peptide continuous infusion is necessary, which in practice is very inconvenient and associated with severe restrictions for the patient.

Interestingly there does exist a key enzyme of the RAS which regulates the relationship between activating Ang II and inactivating Ang 1-7: this enzyme, ACE2, was discovered in 1997, however its principal function as modulator of the RAS was not recognised until 2000. As a membrane-anchored glycoprotein on various organs such as heart, kidney, liver and lung, but also on blood vessels, it converts Ang II to Ang 1-7. The expression of ACE2 is controlled by various stimuli, the underlying mechanisms even today still not having been fully established. Various other reaction pathways involving the cooperation/regulation of ACE2 have already been described. Apart from the conversion of Ang II to Ang 1-7 it is possible that many reactions pathways are not yet known. ACE2 is down-regulated in the presence of inflammatory cytokines, which can subsequently lead to a pathological accumulation of Ang II in the compartments in question and in organ damage.

Inflammatory processes as a result of organ damage or after viral or bacterial infections give rise to the release of inflammatory cytokines which reduce endogenous ACE2 expression and hence the formation of protective Ang 1-7. Reactive Ang II accumulates subsequently and potentiates the budding inflammatory process. The concentration of reactive oxygen species in the tissue also increases. In combination with the proliferative and vascularising properties, an increasingly proliferative climate arises which promotes and amplifies further Ang II accumulation. To escape from this vicious circle, the use of ACE2 activity in accordance with the invention has surprisingly proven successful in inhibiting tumour cell growth. Thus on therapeutic administration of this activity Ang II accumulation can be successfully stopped or even prevented and therefore inflammation and a proliferative environment suppressed: by means of an increased or restored ACE2 activity pathologically increased Ang II concentrations are immediately intercepted. Ang 1-7 is reproduced, and due to its anti-inflammatory effect it also reduces inflammation. Also, due to its property of inhibiting ACE, Ang 1-7 limits the subsequent production of Ang II. Ang 1-7 inhibits cell proliferation and subsequently reduces the expression of AT1R. The use of ACE2 activity is consequently an efficient therapeutic strategy for the treatment of various tumours, as cellular degeneration, the neovascularisation of growing tumours and the metastasis of solid tumours can be halted with it.

The use according to the invention of ACE2 enzyme activity can bring the molecular control systems brought out of balance by the tumour back in the direction of a stable starting position by means of an enzyme activity that is known to the body and therefore is not a foreign property. In contrast to the more artificial "small molecules", the specificity of action of which is usually limited and the degradation products of which can cause problems for patient metabolism, ACE2 enzyme activity is integrated into the equilibrium and control processes of the body in such a way that unexpected side-reactions are highly unlikely. It has also surprisingly been demonstrated that although ACE2 is able to bring the out-of-equilibrium processes back in the direction of the stable starting position, a further effect beyond this equilibrium in the other direction cannot be achieved, despite high dosing of ACE2 activity.

The formal exception of lung cancer from the types of tumour to be treated in accordance with the invention can be attributed to WO 2004/000367 in which the use of ACE2 for the treatment of lung diseases is described. In that patent severe lung damage was observed in ACE2 knockout mice that could be prevented or reduced in such mice by the administration of ACE2. A therapeutic concept for the symptomatic treatment of such lung damage, particularly in acute respiratory distress syndrome (ARDS), was therefore confirmed because similar lung damage is observed in ARDS. Similar lung damage was also known in other lung diseases, and therefore in WO 2004/000367, based on the animal model disclosed there, the use of ACE2 activity was also proposed for other lung diseases, including the treatment of lung cancer. It is clear, however, that the disclosure of WO 2004/000367 does not provide any hints to a person skilled in the art that the proposed use for the treatment of lung cancer should also be extended to other tumour diseases. The disclosure of WO 2004/000367 amounts for a skilled person to nothing more than using ACE2 activity for the treatment or prevention of actual lung damage that can be observed in different lung diseases. WO 2004/000367 does not, however, contain any specific disclosure on the specific and causal treatment of lung cancer or on reducing the growth of the lung tumour or the disintegrated cells of that tumour. The proposal in WO 2004/000367, to achieve an improvement in lung function in lung cancer by means of ACE2, does not therefore offer any technical teaching at all for the present invention, but is merely a formal, random overlapping on certain points in the case of lung cancer.

The present invention is applicable to tumours over a broad spectrum, essentially everywhere where the tumour is accompanied by neovascularisation via Ang II, which is the case in all solid tumours and in many haemopoietic cancers (at least in some stages of such malignant diseases of the blood).

The International Statistical Classification of Diseases and Related Health Problems (ICD-10) classifies malignant tumours according to their location. Preferred groups of tumours to be treated according to the invention are therefore similarly to be assigned to such local groups.

Consequently the tumour to be treated according to the invention is preferably selected from tumours of the reproductive tract, in particular ovarian cancer, testicular cancer, prostate cancer or breast cancer, tumours of the digestive tract, in particular stomach cancer, bowel cancer, rectal carcinoma, pancreatic cancer, oesophageal cancer and liver cancer, renal cancer, melanomas or neuroblastomas (the terms "cancer", "tumour" and "carcinoma" etc. always being used synonymously and always referring to malignant diseases).

The present invention is particularly suitable for the prevention or reduction in the growth of tumour cells. This effect can be used advantageously in combination with known therapy concepts. The ACE2 therapy according to the invention is therefore preferably used in combination with a conventional tumour therapy, particularly in combination with radiotherapy, chemotherapy, hormone therapy, antibody therapy, a targeted therapy such as tyrosine kinase inhibitors, and/or surgical tumour removal. The treatment according to the invention can also be used in a very early stage of tumour diseases, the chances of a cure being considerably increased thereby.

Conventional tumour therapies include surgery, i.e. surgical removal of the tumour and adjacent lymph nodes, radiotherapy (by radioactive substances (e.g. radioactive iodine that is actively absorbed by the thyroid), by X-rays, by proton therapy or ion radiation (radiation with protons or ions which spares the tissue surrounding the tumour), by microwaves (heating up the affected tissue)) and drug therapy (by cytotoxic agents ("chemotherapy"; by which the cancer cells are prevented or stopped from multiplying), by hormone therapy (e.g. by testosterone withdrawal in prostate cancer), by blocking of growth receptor-induced signal transduction, by inhibition of blood vessel growth (anti-angioneogenetic agents) or by immunotherapy (to increase the immune response to tumour cells or with the use of specific (monoclonal) antibodies to tumour antigens or radioimmunotherapy)).

In accordance with the invention ACE2 therapy can also be used in palliative therapy and to improve the quality of life of tumour patients, particularly in the terminal stage of these diseases. Palliative therapy can include the administration of analgesics, ensuring adequate nutrition, inhibition of osteoclasis, increasing haemopoiesis in bone marrow, symptomatic therapies (e.g. dilation of stenoses by balloon dilation or insertion of stents) and physiotherapy of such patients.

Particularly preferably the ACE2 activity according to the invention is used to treat the sequelae or side-effects of tumour therapy, in particular for the treatment of the sequelae of radiotherapy, chemotherapy or tumour surgery. In such cases the ability of ACE2 activity to "calm down" again endogenous regulation systems that have got out of control is in particular of decisive importance.

On the basis of the preferred systemic administration of ACE2 activity and the effect on reducing tumour cell growth the present invention is particularly well suited for preventing the metastasis of tumours.

Preferably tumours are treated in accordance with the invention which are characterised by an increased concentration of angiotensin II in the tumour, in the area surrounding the tumour or in the tumour patient. Elevated Ang II concentrations can be reduced by ACE2 in contrast to ACE inhibitors or AT1R antagonists without any side-effects and so the negative effects of Ang II associated with the tumour are stopped and simultaneously the concentration of Ang 1-7 having an antiproliferative and anti-inflammatory effect is increased.

Preferably malignant effusions, various oedema or increased vascular permeability in the context of tumour diseases are treated in accordance with the present invention.

As mentioned, ACE2 activity is preferably administered in a systemically administrable form, particularly preferably in an intravenously administrable form or in the form of a nasal spray, in particular in liposomal form. However, ACE2 activity can also be administered in a locally administrable form, in particular in an intratumoural or intradermal form. The use of a soluble form of ACE2 is particularly preferred for administration to patients.

"Polypeptide with ACE2 activity", "ACE2 polypeptide", "ACE2" or "ACE2 activity" are understood here to be synonymous with enzymatic activity, which corresponds in the chemical sense to the activity of natural human ACE2. Natural human ACE2 is a membrane-anchored carboxypeptidase which as a receptor is expressed mainly on lung, kidney and heart cells, but also on endothelial cells. ACE2 cleaves various peptide substrates such as apelin, bradykinin and angiotensin I, which is cleaved to angiotensin 1-9, and in particular Ang II, which is cleaved to Ang 1-7. Ang II and Ang 1-7 are—as mentioned—antagonists of the RAS. By controlling the peptide conditions ACE2 is crucially responsible for regulation of vessel thickness and for endothelial permeability and in so doing has an effect on homeostasis of the organism. The expression of ACE2 is cytokine-controlled and is reduced in various inflammatory diseases, which in turn results in pathological enrichment of Ang II, one of the principal substrates of ACE2. "ACE2 activity" according to the present invention refers therefore to a polypeptide ("ACE2 polypeptide") which is at least capable of converting Ang II specifically to Ang 1-7.

Particularly preferred ACE2 polypeptides are fragments of natural human ACE2 which have ACE2 activity, i.e. can convert Ang II to Ang 1-7, and—in relation to natural human ACE2—to the extent of at least 10%, preferably at least 50%, even more preferably at least 100%, in particular at least 150%, in each case relative to molar activity.

It has been found according to the invention that Ang II which is increased in the presence of tumours can be down-regulated by increasing ACE2 activity, causing Ang 1-7 to be made available in situ. With ACE2 according to the invention, both the positive effect of ACE inhibitors and AT1R antagonists is achievable and the positive effect of Ang 1-7 has become usable in patients. Therefore the increase in ACE2 activity in tumour patients is eminently suitable as a treatment for various tumours. For this purpose, exogenous ACE2 can be administered systemically e.g. as a soluble protein, or its endogenous activity can be increased by suitable activators or agonists. Examples of suitable ACE2 activators or ACE2 agonists are described, for example, in WO 2004/000365 and in U.S. Pat. No. 6,194,556 B1. By a suitable therapeutic approach ACE2 expression and hence ACE2 activity can also be increased. For example, by introducing nucleic acids coding for a functional ACE2 enzyme (an ACE2 polypeptide) into the tumour patient, increased ACE2 activities can be established in the patient.

Preferably, however, according to the invention the enzyme activity is self-administered, particularly in the form of a recombinant ACE2 product. The ACE2 product according to the invention is, as mentioned, preferably a soluble form of the human ACE2 enzyme (which is present in the body in membrane-bound form). The human wild type (wt) ACE2 molecule has 805 amino acid residues. Amino acids 1-17 constitute a signal sequence; at the C-terminal end the protein is hydrophobic and is anchored with this end in the membrane. With the soluble form of ACE2 preferably the hydrophobic C-terminal regions are therefore eliminated, the ACE2 polypeptide preferably used according to the invention therefore has no transmembrane domain at the C-terminus. Preferred variants of the ACE2 activity according to the invention used for the treatment of tumours therefore have a deletion of the C-terminal 60 to 200 amino acids. Particularly preferred embodiments include soluble ACE2 polypeptides, the polypeptide chain of which comprises amino acids 18-740 or enzymatically active fragments thereof. A further preferred polypeptide comprises amino acids 18-615 of the ACE2 sequence or enzymatically active fragments thereof.

A preferred form of the ACE2 activity according to the invention is the dimeric form as described in EP 08450052.9. The dimeric form—in contrast to the monomeric form otherwise described in the prior art—is more soluble in similarly charged solutions (e.g. physiological infusion solutions, serum, salt solutions, etc.), has no formation of aggregates, is exposed to reduced protease attack, has an increased half-life and is easier to purify.

The soluble section of ACE2 contains 7 N-glycosylation sites. Incompletely glycosylated ACE2 is not as soluble, tends towards aggregation, is potentially immunogenic and has a shorter half-life. Preferably the dimeric recombinant ACE2 polypeptide in particular is therefore glycosylated at at least 80% of the possible N-glycosylation positions and has a sugar moiety of greater than 10% (% by weight of total ACE2) or 11%, 12%, 13%, 14%, preferably greater than 15% or 16%, 17%, 18%, 19%, in particular greater than 20% or 21%, 22%, 23%, 24% or 25%.

According to EP 08450052.9, a production process was described with which highly pure and active, fully complex glycosylated, dimeric ACE2 can be reproducibly produced. This product is characterised by its high sugar moiety (>20% by weight) and the complex, highly branched nature of the partly negatively charged sugar structures. These have a positive effect on the solubility, bioavailability, purity, activity and pharmacology of the product. By selecting a suitable expression construct, a suitable expression host and an optimised selection strategy, by means of a medium attuned to cell metabolism and by means of meticulous accompanying clone analysis and selection, a cell line was produced which results in the desired product.

In accordance with the invention a recombinant ACE2 polypeptide is preferably used which is glycosylated, the glyco groups of an ACE2 polypeptide monomer having a total of at least 10, 11, 12, 13, 14, 15 or at least 16 sialylic acid residues and the ACE2 polypeptide being present as a dimer. Preferably the dimer contains two zinc ions. By sialylic acid residues are meant in particular residues of the N-acetylneuraminic acid type (Neu5Ac), especially at N- or O-glycosylations (as described in Austrian application A 913/2007 or European application EP 08450052.9).

Preferred ACE2 polypeptides therefore have at least 70%, preferably at least 80%, in particular at least 90%, most preferably 100% of the glycosylated N-glycosylation sites [?for?] sialic acid, preferably the N-glycosylation sites corresponding to Asn53, Asn90, Asn103, Asn322, Asn432, Asn546, Asn690 of the ACE2 sequence are sialysed. In special embodiments an asparagine corresponding to this Asn53, Asn90, Asn103, Asn322, Asn432, Asn546 and/or Asn690 ACE2 sequence is mono-, di, tri- or tetrasialylated either individually or together. In a preferred ACE2 preparation preferably at least 50%, 60%, 70%, 80%, 90%, 95%, 99% or 100% of this amino acid is either mono-, di-, tri- or tetrasialylated.

According to the invention a preparation of recombinant ACE2 polypeptides comprising a dimeric ACE2 polypeptide is preferably used, the proportion of ACE2 polypeptides with a molecular weight of less than 100 kDa, preferably less than 104 kDa, especially preferably less than 108 kDa, particularly less than 112 kDa, particularly preferably less than 117 kDa, most preferably less than 119 kDa, being less than 20%, preferably less than 10%, particularly preferably less than 5%, most preferably less than 1%, and in particular 0%. The proportion is determined e.g. by native gel electrophoresis. Preferably the proportion of ACE2 polypeptides with transmembrane domains is less than 20%, preferably less than 10%, particularly preferably less than 5%, most preferably less than 1%, and in particular is 0%.

Preferably the proportion of ACE2 multimers is less than 20%, preferably less than 10%, particularly preferably less than 5%, most preferably less than 1%, and in particular is 0%. By ACE2 multimers are meant complexes with 3 or more ACE2 polypeptides. Preferably the proportion of ACE2 dimers on ACE2 molecules is at least 10%, 20%, 30%, 40%, 50%, 60%, 70%, 80%, 90%, 95% or at least 99%. In further embodiments, either in combination or independently, the proportion of ACE2 monomers on ACE2 molecules can be at least 10%, 20%, 30%, 40%, 50%, 60%, 70%, 80%, 90%, 95% or at least 99%.

The ACE2 polypeptides to be used in accordance with the invention preferably have a catalytic activity of the ACE2 polypeptide or of the preparation (kkat) of at least 4/s, preferably at least 5/s, particularly preferably at least 6/s, especially preferably at least 7/s, most preferably at least 7.6/s, relative to the conversion of Ang II to Ang 1-7 (angiotensin 1-7). The conversion can be tested in a simple manner in a known way, but in particular as described in the examples of A 913/2000.

According to a preferred embodiment of the present invention it is in the main tumour patients with a poor prognosis who are treated with ACE2 activity according to the invention.

The present invention is explained in more detail by way of the following examples, to which it is of course not restricted.

EXAMPLES

Example 1

Expression of Highly Glycosylated ACE2

The soluble section of the human ACE2 sequence was cloned into an expression vector into which the amplifiable selection marker DHFR had previously been inserted in order to result in increased expression of the ACE2 gene. To this end there was inserted between the genes coding for ACE2 and DFHR an attenuated IRES enabling bicistronic reading of ACE2 and DHFR on the same mRNA. After both proteins are expressed under the control of the same promoter, ACE2 expression can be increased in a targeted way via DHFR selection using the antagonist MTX. By means of this strategy it is possible to obtain particularly stable expression cell lines supplying high yields of a product of constant quality. Even in cell lines this enables reasonable product titres to be achieved that are possibly less suited for recombinant expression of a specific target protein.

This vector was transfected in CHOdhfr- and the number of copies of ACE2 genes was amplified under continuously increasing MTX pressure. Over several rounds of selection and subcloning the best producers were selected by means of intracellular FACS analysis and protein and enzyme analyses for optimum product properties: for choosing the most suitable clone the following were considered in the main: specific enzyme activity measured with 3 different substrates, product homogeneity, cellular productivity, and sugar complexity. The product properties were improved by specific selection of highly glycosylating clones in order to express enzymatically highly active and complex N-glycosylated ACE2.

Whereas soluble ACE2 has a molecular weight of 83 kDa, clones are chosen which appear in the range of up to 120 kDa in the SDS-PAGE, due to their sugar structure. The preliminary clones were then converted to protein-free growth medium. This medium is chemically defined and is suited to the recombinant expression of glycoproteins in CHO. All the clones were kept in culture and checked for their suitability for a production process. In particular, growth rates were recorded and the supernatants examined for product flow and metabolites. Again the products of expression and the clones were closely analysed.

All the clones expressed highly active ACE2 and had productivities around 20-30 pg/cell/day. The sugar structures and their heterogeneity were also analysed. Clones were selected where all 7 N-glycosylation sites in ACE2 were processed, these sites having at least biantenna, and some also having triantenna, complex glycosylation with terminal sialic acids. On the basis of the clone finally selected, a master cell bank was produced and tested, and a GMP compliant purification process and subsequently a GMP production process were set up.

The rACE2 produced according to this example is obtained as a dimer. Due to dimerisation of ACE2, all the hydrophobic protein units are directed into the inside of the complex, the charged residues, such as N-bound sugar chains, jutting outwards and the structure being solvated in a similarly charged physiological environment.

This dimerisation of a fully N-glycosylated ACE2 was ascertained by expression in the presence of $Zn^{2+}$. The dimer complex comprises 2 identical subunits which are bound electrostatically to one another and which no longer separate in physiological solutions. There is secretion of a glycoprotein with 14 strongly charged sialic acid structures on each ACE2 molecule and 28 sialic acid structures in the dimer. Two $Zn^{2+}$ atoms in each case are incorporated into the complex and stabilise its structure. The strong charge of the sugar chains solvates the molecule in physiological aqueous solutions and forces the accompanying charged protein domains outwards. The production process was designed in such a way that exclusively ACE2 dimers occur in the end product. This is made possible by the fact that when generating the rACE2 sufficient $Zn^{2+}$ ions are present (preferably 1.5-5 micromolar $Zn^{2+}$ are used, in particular fermentation can be carried out at 2.5-3.5 µM $Zn^{2+}$) and then the further treatment steps are carried out in the presence of $Zn^{2+}$ ions.

Example 2

Pharmacological Product Properties

The dimer-ACE2 preparation produced according to Example 1 is present as a stable, highly pure and concentrated protein solution in physiological buffer and can be stored and administered with further stabilisation.

This ACE2 does not exhibit any aggregation to multimers owing to the high proportion of sugar. The ACE2 preparation also has full enzyme activity.

Owing to its solubility, ACE2 can be administered i.v. as a bolus, as well as subcutaneously. For the same reasons bioavailability is guaranteed systemically immediately after administration.

ACE2 is metabolised slowly due to the large, highly branched and complex sugar moiety. This results in a long terminal half-life of at least 10.5 hours which was measured in various species, including rhesus monkeys.

The high sialic acid moiety also means that no neutralising immune response is built up against ACE2 in humans. This would not only be counterproductive for the exogenous administration of ACE2, but could also neutralise autologous intracellular ACE2. The ACE2 formulation described, together with all accompanying product properties, therefore enables for the first time an efficient treatment with rhACE2.

Example 3

Determination of Specific ACE2 Activity

The specific activity of ACE2 preparations was determined by measuring the conversion of Ang II (Asp-Arg-Val-Tyr-Ile-His-Pro-Phe). All the measurements were carried out as triple determinations in a batch volume of 100 µl. The enzymatic reaction was started by adding 250 ng/ml ACE2 to an 80 µM Ang II solution in 50 mM MES, 300 mM NaCl, 10 µM $ZnCl_2$ and 0.01% Brij 30 at pH 6.5. The samples were carefully mixed and incubated for precisely 18 minutes at 37° C. The enzymatic reaction was stopped by adding 100 mM EDTA. For analysis, the solutions were separated by means of RP-HPLC (Waters C18 µBondapak, 2.1×300 mm, 10 µm, 125 Å) using a linear gradient of 10 to 60% $CH_3CN$ in 0.08% $H_3PO_4$ for 20 minutes at a flow rate of 1 ml/min. Furthermore, both Ang II and Ang 1-7 peaks were recognised and integrated in the chromatograms. The peptide concentrations were determined using calibration curves. Enzymatic conversion and specific enzyme activity were also determined.

The ACE2 preparation produced according to Example 1 has a catalytic activity kkat of 8.0±0.3/s based on Ang II conversion and 8.8±0.2/s in relation to Ang 1-7 conversion. Both values correspond well and are clearly higher than the figures of Vickers et al. (J. Biol. Chem. 2002 277 (17): 14838-43) who published a catalytic ACE2 activity of 3.5/s. The reactions conditions were identical.

The cause of the 240% higher activity according to the present preparation would seem to be post-translational modifications and in this instance primarily N-glycosylation, which was significantly less pronounced in the material used by Vickers. The material described there was expressed in insect cells and although it had the same amino acid sequence was glycosylated to a considerably lesser extent and to a considerably lower degree of branching. A commercially available ACE2 preparation from R&D systems (cat. 933-ZN), which also had considerably lower kkat activity of 2.0±0.1/s, was also investigated. An important characteristic of the dimer preparation preferably to be used according to the invention is therefore the astonishingly high activity that is made possible in the main by post-translational modifications.

Example 4

Suppression of Tumour Cell Growth

A human tumour cell line was sowed at a density of 2.5× $10^4$ cells/ml in 200 µl RPMI 1640 in 10% FCS in 96-well plates and incubated at 37° C. and 5% $CO_2$. The influence of various active components of the RAS were evaluated using the following test systems. All the analyses were carried out as triple determinations (sACE2=soluble ACE2 without C-terminal membrane domain):

Condition A. Culture medium RPMI 1640 with 10% FCS as control
Condition B. Culture medium supplemented with 100 nM Ang II
Condition C. Culture medium supplemented with 100 nM Ang 1-7
Condition D. Culture medium supplemented with 20 μg/ml sACE2
Condition E. Culture medium supplemented with 20 μg/ml sACE2 and 100 mM Ang II Every day 100 μl of medium was removed and replaced by the same volume of fresh specific medium. The cell count was determined on days 2, 3, 6, 8, 10, 13, 15 and 17 by multiple counting in a haemocytometer. A separately prepared test plate was used for each determination.

Significant differences in the cell count determination caused by differing growth conditions were visible from the fourth day of culture onwards. The addition of Ang II caused distinctly increased cell growth. Ang 1-7 on the other hand reduced cell growth. Whereas ACE2 alone (understandably due to lack of substrate) induced marginally increased growth, the addition of ACE2 in the presence of Ang II reduced cell growth, in a similar way as by the addition of Ang 1-7 alone. ACE2 therefore not only neutralised the increased cell growth induced by Ang II, but inhibited it via effects of the peptide Ang 1-7. This was evidently only formed when, besides ACE2, Ang II was also added to the growth medium.

Therefore it has also been shown with this example that ACE2 can suppress the "activating" Ang II track and build up the "attenuating" Ang 1-7 side. As demonstrated experimentally, both effects cause tumour cell growth to be slowed down.

The invention claimed is:

1. A method of treating tumor diseases other than lung cancer comprising administering to a human patient in need thereof a recombinant, human, water-soluble, glycosylated with a sugar content greater than 10% by weight of total ACE2, dimeric angiotensin-converting-enzyme-2 (ACE2) polypeptide with ACE2 activity, wherein said recombinant, human, water-soluble, glycosylated with a sugar content greater than 10% by weight of total ACE2, dimeric ACE2 polypeptide comprises amino acids 18-740 of human wild type 805 amino acid ACE2, and wherein the tumor diseases are characterized by an increased angiotensin-II concentration in the tumor or in the tumor environment or in the tumor patient.

2. The method according to claim 1, wherein the tumor disease is selected from tumor diseases of the reproductive tract selected from the group consisting of: ovarian cancer, testicular cancer, prostate cancer or breast cancer, tumor diseases of the digestive tract, stomach cancer, intestinal cancer, rectum carcinoma, pancreatic cancer, esophagus cancer and liver cancer, kidney cancer, melanomas and neuroblastomas.

3. The method according to claim 1, wherein the recombinant, human, water-soluble, glycosylated with a sugar content greater than 10% by weight of total ACE2, dimeric ACE2 polypeptide is administered in combination with known therapy concepts selected from the group consisting of: radiotherapy, chemotherapy, hormone therapy, antibody therapy, a targeted therapy and surgical tumour removal, and wherein the polypeptide is used for the treatment of the effects, or side-effects, of the known therapy concepts.

4. The method according to claim 1, wherein the tumor disease is tumor metastasis.

5. The method according to claim 1, wherein the tumor disease is selected from the group consisting of: malignant effusions, edemas and increased vascular permeability associated with the tumor diseases.

6. The method according to claim 1, wherein the recombinant, human, water-soluble, glycosylated with a sugar content greater than 10% by weight of total ACE2, dimeric ACE2 polypeptide is administered in a form selected from the group consisting of: a systemically applicable form, an intravenously applicable form, a nasal spray, and a liposomal form.

7. The method according to claim 1, wherein the recombinant, human, water-soluble, glycosylated with a sugar content greater than 10% by weight of total ACE2, dimeric ACE2 polypeptide is administered in a form selected from the group consisting of: a locally applicable form, intratumorous form, subcutaneous form and intradermal form.

8. The method according to claim 1, wherein the recombinant, human, water-soluble, glycosylated with a sugar content greater than 10% by weight of total ACE2, dimeric ACE2 polypeptide is used in combination with conventional tumor therapy, wherein the conventional tumor therapy is selected from the group consisting of: radiotherapy, chemotherapy, antibody therapy and surgical tumor removal.

9. The method according to claim 1, wherein the tumor disease is characterized by a negative prognosis for the patient.

* * * * *